United States Patent [19]

Crowninshield et al.

[11] Patent Number: 5,219,363
[45] Date of Patent: Jun. 15, 1993

[54] BONE IMPLANT

[75] Inventors: Roy D. Crowninshield; Thirumalai N. C. Devanathan; Howard C. Price; Abner K. Wang, all of Warsaw; Jack E. Parr, North Webster, all of Ind.

[73] Assignee: Zimmer, Inc., Warsaw, Ind.

[21] Appl. No.: 399,406

[22] Filed: Aug. 25, 1989

Related U.S. Application Data

[63] Continuation of Ser. No. 171,626, Mar. 22, 1988, abandoned.

[51] Int. Cl.$^5$ .......................... A61F 2/32; A61F 2/28
[52] U.S. Cl. ......................................... 623/23; 623/16
[58] Field of Search .................. 623/22, 23, 8

[56] References Cited

U.S. PATENT DOCUMENTS

| | | |
|---|---|---|
| 3,662,405 | 7/1972 | Bootz et al. . |
| 3,905,777 | 9/1975 | Lacroix ........................ 128/92 R X |
| 3,938,198 | 6/1976 | Kahn et al. . |
| 4,237,559 | 3/1980 | Borom . |
| 4,356,571 | 8/1982 | Esper et al. . |
| 4,454,612 | 6/1984 | McDaniel et al. ..................... 623/23 |
| 4,479,271 | 3/1984 | Bolesky et al. . |
| 4,535,485 | 11/1985 | Ashman et al. . |
| 4,536,894 | 8/1985 | Galante et al. ........................ 623/22 |
| 4,636,219 | 1/1987 | Pratt et al. ............................ 623/22 |
| 4,662,887 | 5/1987 | Turner et al. ......................... 623/16 |
| 4,714,467 | 12/1987 | Lechner et al. ....................... 623/16 |
| 4,750,905 | 6/1988 | Koeneman et al. ................... 623/16 |
| 4,778,469 | 10/1988 | Lin et al. .............................. 623/16 |
| 4,813,960 | 3/1989 | Muller ................................... 623/22 |
| 4,976,738 | 12/1990 | Frey et al. ......................... 623/23 X |

FOREIGN PATENT DOCUMENTS

| | | |
|---|---|---|
| 0016480 | 1/1980 | European Pat. Off. . |
| 2163960 | 7/1986 | United Kingdom . |

OTHER PUBLICATIONS

Evaluation of a Metal-Cermic Composite Hip Prosthesis S.F. Hulbert et al, J. Biomed Motor Res Symposium (1975) (pp. 189-198).
Potential of Ceramic Materials & Permanently Implantable Skeletal Prosthesis, S. F. Hulbert et al, J Biomed Motor Res (1970) (pp. 433-456).
Harris/Galante Porous Hip Prosthesis, Ad, Zimmer ©1986.
Methodology for Development of a Composite Material Hip Replacement, Ainsworth (undated).

*Primary Examiner*—David Isabella
*Attorney, Agent, or Firm*—Paul David Schoenle

[57] ABSTRACT

A bone implant includes a nonmetallic core and a metallic porous surface secured to the nonmetallic core. The nonmetallic core is designed to closely approximate the modulus of elasticity for bone and the metallic porous surface is intimately engaged with bone to enhance bone growth into the metallic porous surface.

1 Claim, 1 Drawing Sheet

BONE IMPLANT

This application is a continuation of application Ser. No. 07/171,626, filed Mar. 22, 1988 now abandoned.

The present invention relates to a bone implant which is used in a surgical proceeding to repair or reconstruct skeletal deformities. These bone implants have been utilized by orthopaedic surgeons in hip and knee arthroplasty to reconstruct articulating joints, as well as in trauma situations to secure fractured bones together.

Various metals have been proposed to manufacture bone implants. Titanium and cobalt chrome, for example, are in wide spread use because of their biocompatibility with bone tissue and their strength characteristics for carrying loads imparted to the skeletal structure following implantation. With a metal bone implant, U.S. Pat. Nos. 3,605,123 and 3,900,550 further provide a porous metallic surface to enhance fixation of the implant with a resected bone at the intramedullary canal. These metals are stronger than bone; however, bone is somewhat flexible, and the stiff metals do not exactly match the flexibility of bone. As a result, numerous recent articles and patents are proposing the use of composites or nonmetals for the construction of bone implants in order to provide the implant with a modulus substantially the same as bone.

In U.S. Pat. No. 4,662,887 a polyetheretherketone commonly referred to as PEEK is disclosed for use as an orthopaedic device. The PEEK polymer is biocompatible and sufficiently flexible in final form to approximate the anatomic elasticity of bone. In Hochman U.S. Pat. No. 3,893,196, a composite hip implant is provided with a graphite fiber core, an outer layer of graphite fiber circumscribing the core and a plastic skin enclosing all of the fiber and providing a porous plastic surface to enable the bone to knit thereto. In further support of Hochman is U.S. Pat. No. 4,164,794, wherein a porous composite material is provided on the surface of a hip prosthesis to enhance fixation to bone.

Comparing the metal implant with the composite implant, advantages and disadvantages are apparent. With the metal implant, the strength characteristics of metals results in a stiff implant which may stress shield portions of the bone. To date, no composite implant has established the intimate bone association believed to be necessary for adherence to bone for long term fixation in spite of the numerous attempts to provide a porous composite surface for the composite implant. Further it is believed that polymer surfaces may be insufficiently durable to transfer load and posses inadequate abrasion resistance for long term fixation.

The present invention teaches an orthopaedic implant which incorporates the advantages of metal and composite materials. Rather than relying upon a total composite or a total metal implant, the invention provides a composite core which closely approximates the flexibility of bone and a porous metallic surface secured to the composite core so that bone growth and/or cement will readily penetrate and adhere to the porous metallic surface for long term fixation of the orthopaedic implant.

It is an advantage of the present invention that the composite/metal implant approximates the flexibility of bone and provides a porous metallic surface which is readily compatible with bone to provide unrestricted ingrowth of bone into the porous surface and such porous metallic surface is sufficiently strong and durable to provide for long term fixation. Moreover, the porous metallic surface is provided by a metallic fiber metal pad which resists abrasion and remains integrally secured to the composite core during implantation as well as after implantation.

In the drawings, FIG. 1 is a side view of a femoral component following implantation.

Figure 1:
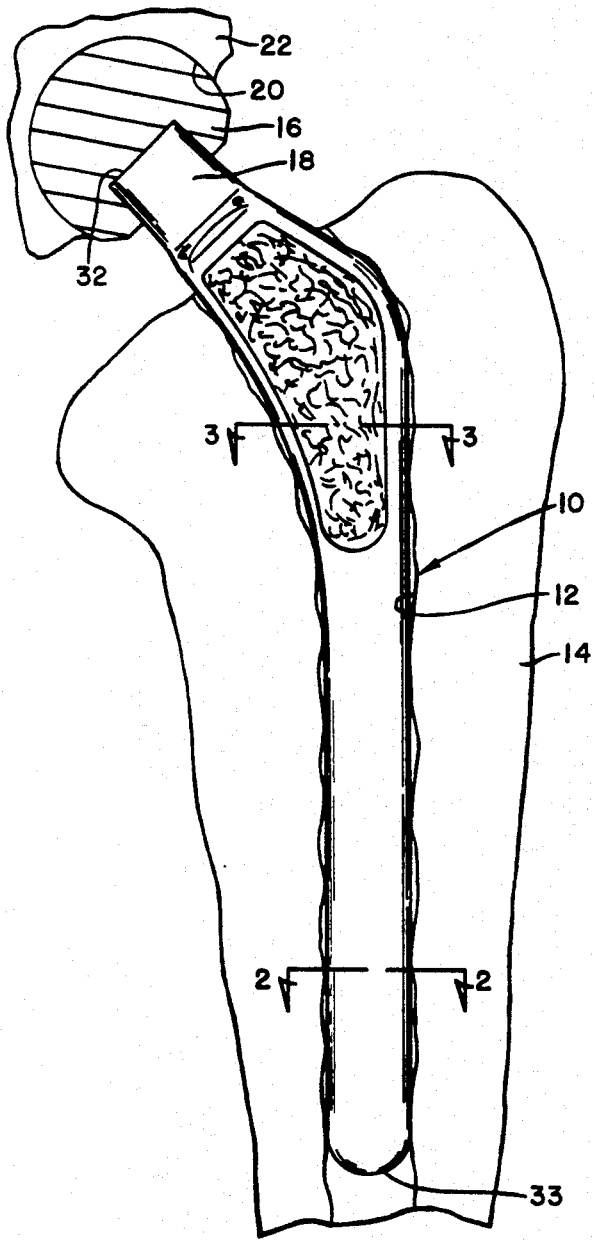
Figure 2:
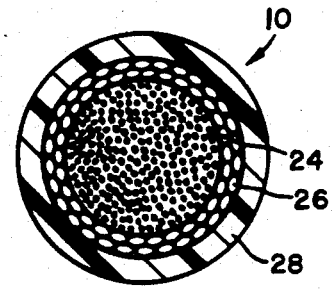
FIG. 2 is a cross sectional view taken along line 2—2 of FIG. 1.

The femoral component 10 is surgically implanted into the intramedullary canal 12 of the femur 14. The intramedullary canal 12 is exposed by resection of the anatomic femoral head (not shown). A head 16 is coupled to a neck 18 of the femoral component. The head 16 is spherical in shape to provide for articulation within a socket 20 of an acetabulum 22.

The femoral component 10 includes a core 24 comprising a plurality of longitudinally extending fibers, an intermediate layer 26 comprising a braided sheath of fibers, a skin 28 enclosing the core 24 and intermediate layer 26, and a pair of porous fiber metal pads 30 and 31 secured to the skin 28. In the drawings the intermediate layer 26 is shown as a larger fibercross section than the core 24 for illustration purposes only. The core 24 and intermediate layer 26 are constructed from the same fibers.

The core 24, intermediate layer 26 and skin 28 extend from a distal end 33 to a proximal end 32 forming the neck 18. The porous fiber metal pads 30 and 31 are preferably disposed adjacent the neck 18 and on both sides, anteriorly and posteriorly, of the femoral component.

The plurality of fibers forming the core 24 and the braided sheath of fibers forming the intermediate layer 26 are made of APC-2 as sold by FIBERITE, an Imperial Chemical Industry affiliate, see FIBERITE® Data Sheet 3a propriety data of aromatic polymer composite, APC-2/Hercules Magnamite® AS4 Carbon Fibre. This material includes continuous carbon fibre with PEEK impregnated into the continuous carbon fibre.

The skin 28 is made of polyetheretherketone or PEEK as taught by U.S. Pat. No. 4,662,887. This material is available from Imperial Chemical Industries per the specification for Victrex® 450G polyetheretherketone (PEEK) natural color granular molding resin.

The fiber metal pads 30 and 31 are disclosed in U.S. Pat. No. 3,906,550 as short titanium wires which are kinked in a sinusoidal pattern with a specific amplitude to period ratio of 0.24. Numerous short wires are sintered together to form a unitary porous pad for fixation to the skin 28.

In order to manufacture the femoral component 10, the longitudinal fibers for the core 24 are bundled together and pulled through braiders for braiding a sheath or layer 26 over the core 24. With the sheath or layer covering the core 24, a suitable length is cut and disposed in a mold so that the skin 28 can be injection molded over the sheath 26 and core 24. The PEEK material for the skin 28 is heated in the injection molding step and readily attaches to the impregnated PEEK in the carbon fibers of the sheath 26 and the core 24.

Figure 3:
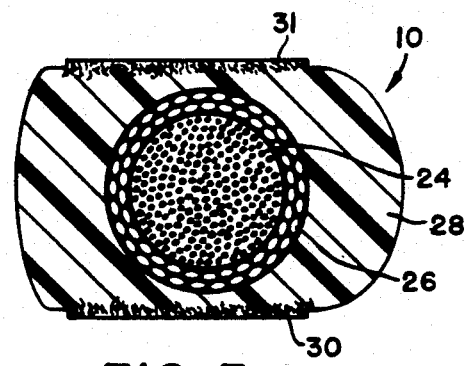
FIG. 3 is a cross sectional view taken along line 3—3 of FIG. 1.
Figure 4:
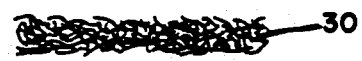
FIG. 4 is a cross sectional view of the porous fiber metal pad separate from the composite stem.

After the skin is cooled, a fiber metal pad as shown in FIG. 4 is heated to a temperature sufficient to permit the skin to penetrate the heated pad. It is believed that a temperature of about 600° F. suffices for penetration. A heated fiber metal pad is then forced into each side of the stem to penetrate via melting into the skin 28 a predetermined distance. Preferably, one-half of the thickness of the fiber metal pad is penetrated into the skin as seen in comparing FIGS. 3 and 4. When the fiber metal pad cools, the penetrated portion of the fiber metal pad is trapped within or secured to the skin 28 while an outer portion of the fiber metal pad remains porous or open for intimate contact with bone and the resulting bony ingrowth that follows in view of the affinity for bone to associate with titanium wire.

Figure 5:
FIG. 5 is a view similar to FIG. 3 showing an alternative embodiment of the invention.

In the alternative embodiment of FIG. 5, a metal barrier 40 separates the fiber metal pads 30 into an inner fiber metal portion 42 and an outer fiber metal portion 44. The barrier 40 separates that portion of the pad intended for impregnation into the skin from that portion of the fiber metal pad intended for bony ingrowth.

Although the aforegoing description proceeds with reference to PEEK and titanium fiber metal pad, it is contemplated that other composite cores with or without fiber reinforcement can be utilized with other types of metallic porous surfaces, e.g. beads, to generate a hybrid composite/metal bone implant that includes a modulus substantially the equivalent of bone and a porous metallic surface to encourage bone ingrowth. Prosthetic knee components can also be made by the composite/metal bone implant of the present invention. In addition, the composite bone implant with the porous metallic surface of the present invention, is also readily adapted for use in a cemented hip arthroplasty where PMMA bone cement is used to secure the implant to bone.

The material for the skin 28 is referred to hereinabove as polyetheretherketone or PEEK; however, such material is also referred to as polyaryletherketone. As an alternative material, it is believed that polyetherketone (PEK) or polyetherketoneketone (PEKK) is suitable for forming the skin and as a matrix for the carbon fibers of the core and braid. The polyetheraketone (PEK) is available from Imperial Chemical Industries and the polyetherketoneketone is available from DuPont as PEKK polymer. As such this material is also included in the invention claimed.

We claim:

1. A femoral hip component adapted to implantation within a femoral canal of a bone, the femoral canal being open at one end in response to resection of a femoral head of the bone, the femoral hip component comprising a nonmetallic core extending into the femoral canal and opposing the wall thereof to substantially fill the femoral canal, the nonmetallic core being flexible to substantially approximate the flexibility of the bone surrounding the femoral canal, and a porous metallic component fixedly secured to the nonmetallic core for disposition at an outer surface of the nonmetallic core in intimate contact with the wall of the femoral canal to accommodate bone growth when the femoral hip component is implanted into the femoral canal, the porous metallic component including a substantially nonporous barrier embedded therein and the nonmetallic core extends into the metallic porous surface component up to but not past the nonporous barrier.

* * * * *